(12) United States Patent
Blumzvig et al.

(10) Patent No.: US 8,194,121 B2
(45) Date of Patent: Jun. 5, 2012

(54) MINIATURE CAMERA HEAD

(75) Inventors: Arie Blumzvig, Netanya (IL); Alex Zaretsky, Nesher (IL); Doron Adler, Nesher (IL); Frank D'Amelio, Los Olivos, CA (US)

(73) Assignee: C2Cure, Inc., Wilmington, DE (US)

( * ) Notice: Subject to any disclaimer, the term of this patent is extended or adjusted under 35 U.S.C. 154(b) by 1252 days.

(21) Appl. No.: 10/514,607

(22) PCT Filed: May 15, 2003

(86) PCT No.: PCT/IL03/00399
§ 371 (c)(1),
(2), (4) Date: Jul. 20, 2005

(87) PCT Pub. No.: WO03/098913
PCT Pub. Date: Nov. 27, 2003

(65) Prior Publication Data
US 2005/0267328 A1      Dec. 1, 2005

Related U.S. Application Data

(60) Provisional application No. 60/381,478, filed on May 16, 2002.

(51) Int. Cl.
*A62B 1/04* (2006.01)
*A61B 1/04* (2006.01)
(52) U.S. Cl. .......................................... 348/65; 348/76
(58) Field of Classification Search .................... 348/42, 348/45–49, 51, 61–68
See application file for complete search history.

(56) References Cited

U.S. PATENT DOCUMENTS

| | | |
|---|---|---|
| 3,321,656 A | 5/1967 | Sheldon |
| 3,971,065 A | 7/1976 | Bayer |
| 4,253,447 A | 3/1981 | Moore et al. |
| 4,261,344 A | 4/1981 | Moore et al. |
| 4,278,077 A | 7/1981 | Mizumoto |
| 4,429,328 A | 1/1984 | Jones, Jr. et al. |
| 4,467,361 A | 8/1984 | Ohno et al. |
| 4,491,865 A | 1/1985 | Danna et al. |
| 4,555,768 A | 11/1985 | Lewis, Jr. et al. |

(Continued)

FOREIGN PATENT DOCUMENTS
CA            2173113 A1      4/1995
(Continued)

OTHER PUBLICATIONS

NORIKA3—http://www.rfnorika.com—Dec. 24, 2001 (website printed Jan. 1, 2002) 14 pages.

(Continued)

*Primary Examiner* — David Czekaj
(74) *Attorney, Agent, or Firm* — Ganz Law, P.C.

(57) ABSTRACT

An electronic imaging device (27) includes an optical objective (28) for collecting optical radiation from an object, the objective having an optical axis, and an image sensor (24), including a matrix of optical detectors arranged in a plane that is substantially non-perpendicular to the optical axis, the image sensor having a lateral dimension in the plane. A turning mirror (38) has an optical surface that is positioned so as to reflect the radiation collected by the objective in order to form a focused image in the plane of the image sensor, while a maximum distance from the optical surface to the plane of the image sensor is substantially less than the lateral dimension of the image sensor.

72 Claims, 6 Drawing Sheets

U.S. PATENT DOCUMENTS

| | | | |
|---|---|---|---|
| 4,569,335 A | 2/1986 | Tsuno | |
| 4,573,450 A | 3/1986 | Arakawa | |
| 4,576,146 A | 3/1986 | Kawazoe et al. | |
| 4,602,281 A | 7/1986 | Nagasaki et al. | |
| 4,604,992 A | 8/1986 | Sato | |
| 4,625,236 A | 11/1986 | Fujimori et al. | |
| 4,633,304 A | 12/1986 | Nagasaki | |
| 4,646,721 A | 3/1987 | Arakawa | |
| 4,651,201 A | 3/1987 | Schoolman | |
| 4,656,508 A | 4/1987 | Yokota | |
| 4,682,219 A | 7/1987 | Arakawa et al. | |
| 4,692,608 A | 9/1987 | Cooper et al. | |
| 4,697,208 A | 9/1987 | Eino | |
| 4,713,683 A | 12/1987 | Fujimori et al. | |
| 4,714,319 A | 12/1987 | Zeevi et al. | |
| 4,720,178 A | 1/1988 | Nishioka et al. | |
| 4,741,327 A | 5/1988 | Yabe | |
| 4,746,203 A | 5/1988 | Nishioka et al. | |
| 4,757,805 A | 7/1988 | Yabe | |
| 4,768,513 A | 9/1988 | Suzuki | |
| 4,784,133 A | 11/1988 | Mackin | |
| 4,803,550 A | 2/1989 | Yabe et al. | |
| 4,803,562 A | 2/1989 | Eino | |
| 4,809,680 A | 3/1989 | Yabe | |
| 4,819,065 A | 4/1989 | Eino | |
| 4,827,907 A | 5/1989 | Tashiro | |
| 4,827,909 A | 5/1989 | Kato et al. | |
| 4,831,456 A | 5/1989 | Takamura et al. | |
| 4,832,003 A | 5/1989 | Yabe | |
| 4,832,033 A | 5/1989 | Maher et al. | |
| 4,857,724 A | 8/1989 | Snoeren | |
| 4,862,873 A | 9/1989 | Yajima et al. | |
| 4,866,526 A | 9/1989 | Ams et al. | |
| 4,869,256 A | 9/1989 | Kanno et al. | |
| 4,873,572 A | 10/1989 | Miyazaki et al. | |
| 4,884,133 A | 11/1989 | Kanno et al. | |
| 4,905,670 A | 3/1990 | Adair | |
| 4,926,257 A | 5/1990 | Miyazaki | |
| 4,934,339 A | 6/1990 | Kato | |
| 4,939,573 A | 7/1990 | Teranishi et al. | |
| 4,953,539 A | 9/1990 | Nakamura et al. | |
| 4,967,269 A | 10/1990 | Sasagawa et al. | |
| 4,986,642 A | 1/1991 | Yokota et al. | |
| 4,998,972 A | 3/1991 | Chin et al. | |
| 5,010,875 A | 4/1991 | Kato | |
| 5,021,888 A | 6/1991 | Kondou et al. | |
| 5,022,399 A | 6/1991 | Biegeleisen | |
| 5,029,574 A | 7/1991 | Shimamura et al. | |
| 5,122,650 A | 6/1992 | McKinley | |
| 5,166,787 A | 11/1992 | Irion | |
| 5,184,223 A | 2/1993 | Mihara | |
| 5,187,572 A * | 2/1993 | Nakamura et al. | 348/68 |
| 5,191,203 A | 3/1993 | McKinley | |
| 5,216,512 A | 6/1993 | Bruijns et al. | |
| 5,222,477 A | 6/1993 | Lia | |
| 5,233,416 A | 8/1993 | Inoue | |
| 5,264,925 A | 11/1993 | Shipp et al. | |
| 5,301,090 A | 4/1994 | Hed | |
| 5,311,600 A | 5/1994 | Aghajan et al. | |
| 5,323,233 A | 6/1994 | Yamagami et al. | |
| 5,325,847 A | 7/1994 | Matsuno | |
| 5,335,662 A | 8/1994 | Kimura et al. | |
| 5,343,254 A | 8/1994 | Wada et al. | |
| 5,363,135 A | 11/1994 | Inglese | |
| 5,376,960 A | 12/1994 | Wurster | |
| 5,408,268 A | 4/1995 | Shipp | |
| 5,430,475 A * | 7/1995 | Goto et al. | 348/65 |
| 5,432,543 A | 7/1995 | Hasegawa et al. | |
| 5,444,574 A | 8/1995 | Ono et al. | |
| 5,450,243 A | 9/1995 | Nishioka | |
| 5,471,237 A | 11/1995 | Shipp | |
| 5,494,483 A | 2/1996 | Adair | |
| 5,498,230 A | 3/1996 | Adair | |
| 5,512,940 A | 4/1996 | Takasugi et al. | |
| 5,547,455 A | 8/1996 | McKenna et al. | |
| 5,557,324 A | 9/1996 | Wolff | |
| 5,575,754 A | 11/1996 | Konomura | |
| 5,594,497 A | 1/1997 | Ahern et al. | |
| 5,598,205 A | 1/1997 | Nishioka | |
| 5,603,687 A | 2/1997 | Hori et al. | |
| 5,604,531 A | 2/1997 | Iddan et al. | |
| 5,607,436 A * | 3/1997 | Pratt et al. | 606/143 |
| 5,668,596 A | 9/1997 | Vogel | |
| 5,673,147 A | 9/1997 | McKinley | |
| 5,700,236 A | 12/1997 | Sauer et al. | |
| 5,712,493 A | 1/1998 | Mori et al. | |
| 5,728,044 A | 3/1998 | Shan | |
| 5,751,341 A | 5/1998 | Chaleki et al. | |
| 5,754,280 A | 5/1998 | Kato et al. | |
| 5,792,045 A | 8/1998 | Adair | |
| 5,797,837 A | 8/1998 | Minami | |
| 5,819,736 A | 10/1998 | Avny et al. | |
| 5,847,394 A | 12/1998 | Alfano et al. | |
| 5,905,597 A | 5/1999 | Mizouchi et al. | |
| 5,907,178 A | 5/1999 | Baker et al. | |
| 5,928,137 A | 7/1999 | Green | |
| 5,929,901 A | 7/1999 | Adair et al. | |
| 5,940,126 A | 8/1999 | Kimura | |
| 5,944,655 A | 8/1999 | Becker | |
| 5,984,860 A | 11/1999 | Shan | |
| 5,986,693 A | 11/1999 | Adair et al. | |
| 6,001,084 A | 12/1999 | Riek et al. | |
| 6,006,119 A * | 12/1999 | Soller et al. | 600/322 |
| 6,009,189 A | 12/1999 | Schaack | |
| 6,010,449 A | 1/2000 | Selmon et al. | |
| 6,039,693 A | 3/2000 | Seward et al. | |
| 6,043,839 A | 3/2000 | Adair et al. | |
| 6,075,235 A | 6/2000 | Chun | |
| 6,099,475 A | 8/2000 | Seward et al. | |
| 6,124,883 A * | 9/2000 | Suzuki et al. | 348/68 |
| 6,129,672 A | 10/2000 | Seward et al. | |
| 6,134,003 A | 10/2000 | Tearney et al. | |
| 6,139,490 A | 10/2000 | Breidenthal et al. | |
| 6,142,930 A | 11/2000 | Ito et al. | |
| 6,148,227 A | 11/2000 | Wagnieres et al. | |
| 6,177,984 B1 | 1/2001 | Jacques | |
| 6,178,346 B1 | 1/2001 | Amundson et al. | |
| 6,184,923 B1 | 2/2001 | Miyazaki | |
| 6,206,825 B1 | 3/2001 | Tsuyuki | |
| 6,240,312 B1 | 5/2001 | Alfano et al. | |
| 6,260,994 B1 | 7/2001 | Matsumoto et al. | |
| 6,281,506 B1 | 8/2001 | Fujita et al. | |
| 6,284,223 B1 | 9/2001 | Luiken | |
| 6,327,374 B1 | 12/2001 | Piironen et al. | |
| 6,331,156 B1 | 12/2001 | Haefele et al. | |
| 6,409,658 B1 | 6/2002 | Mitsumori | |
| 6,416,463 B1 | 7/2002 | Tsuzuki et al. | |
| 6,449,006 B1 | 9/2002 | Shipp | |
| 6,459,919 B1 | 10/2002 | Lys et al. | |
| 6,464,633 B1 | 10/2002 | Hosoda et al. | |
| 6,476,851 B1 | 11/2002 | Nakamura | |
| 6,485,414 B1 | 11/2002 | Neuberger | |
| 6,533,722 B2 | 3/2003 | Nakashima | |
| 6,547,721 B1 | 4/2003 | Higuma et al. | |
| 6,659,940 B2 | 12/2003 | Adler | |
| 6,670,636 B2 | 12/2003 | Hayashi et al. | |
| 6,692,430 B2 | 2/2004 | Adler | |
| 6,697,110 B1 | 2/2004 | Jaspers et al. | |
| 6,943,837 B1 | 9/2005 | Booth, Jr. | |
| 6,976,956 B2 * | 12/2005 | Takahashi et al. | 600/166 |
| 6,984,205 B2 | 1/2006 | Gazdzinski | |
| 7,030,904 B2 * | 4/2006 | Adair et al. | 348/76 |
| 7,106,910 B2 | 9/2006 | Acharya et al. | |
| 7,116,352 B2 | 10/2006 | Yaron | |
| 7,123,301 B1 | 10/2006 | Nakamura et al. | |
| 7,127,280 B2 | 10/2006 | Dauga | |
| 7,133,073 B1 | 11/2006 | Neter | |
| 7,154,527 B1 | 12/2006 | Goldstein et al. | |
| 7,308,296 B2 | 12/2007 | Lys et al. | |
| 7,347,817 B2 | 3/2008 | Glukhovsky et al. | |
| 7,355,625 B1 | 4/2008 | Mochida et al. | |
| 2001/0017649 A1 | 8/2001 | Yaron | |
| 2001/0031912 A1 | 10/2001 | Adler | |
| 2001/0040211 A1 | 11/2001 | Nagaoka | |
| 2001/0051766 A1 | 12/2001 | Gazdzinski | |
| 2002/0089586 A1 | 7/2002 | Suzuki et al. | |
| 2002/0103417 A1 | 8/2002 | Gazdzinski | |

| | | | |
|---|---|---|---|
| 2002/0154215 | A1* | 10/2002 | Schechterman et al. ........ 348/51 |
| 2002/0198439 | A1 | 12/2002 | Mizuno |
| 2003/0171648 | A1 | 9/2003 | Yokoi et al. |
| 2003/0171649 | A1 | 9/2003 | Yokoi et al. |
| 2003/0171652 | A1 | 9/2003 | Yokoi et al. |
| 2003/0174208 | A1 | 9/2003 | Glukhovsky et al. |
| 2003/0174409 | A1 | 9/2003 | Nagaoka |
| 2004/0019255 | A1 | 1/2004 | Sakiyama |
| 2005/0165279 | A1 | 7/2005 | Adler et al. |
| 2005/0259487 | A1 | 11/2005 | Glukhovsky et al. |
| 2006/0158512 | A1 | 7/2006 | Iddan et al. |

FOREIGN PATENT DOCUMENTS

| | | | |
|---|---|---|---|
| DE | 3529026 | | 2/1986 |
| DE | 3720624 | | 1/1989 |
| DE | 19532095 | | 8/1996 |
| DE | 19800312 | | 7/1999 |
| EP | 0630056 | | 12/1994 |
| EP | 434793 | B1 | 4/1995 |
| EP | 0827908 | A1 | 3/1998 |
| EP | 0928597 | | 7/1999 |
| EP | 1326432 | | 7/2003 |
| JP | 5745833 | | 3/1982 |
| JP | 61018915 | A | 7/1984 |
| JP | 60258515 | | 5/1985 |
| JP | 60104915 | | 6/1985 |
| JP | 61-281680 | | 12/1986 |
| JP | 62-35314 | | 3/1987 |
| JP | 63244011 | A | 3/1987 |
| JP | 63-136781 | | 6/1988 |
| JP | 63200115 | | 8/1988 |
| JP | 63-210813 | | 9/1988 |
| JP | 64-068712 | | 3/1989 |
| JP | 01-238853 | | 9/1989 |
| JP | 4236934 | A | 1/1991 |
| JP | 3264043 | A | 11/1991 |
| JP | 4109927 | | 4/1992 |
| JP | HEI4109927 | | 4/1992 |
| JP | 5015515 | | 1/1993 |
| JP | 5142484 | | 6/1993 |
| JP | 5307144 | | 11/1993 |
| JP | 06222283 | A2 | 12/1993 |
| JP | 7163517 | A | 12/1993 |
| JP | 06335450 | | 12/1994 |
| JP | 8220448 | A | 2/1995 |
| JP | 7318815 | A | 6/1995 |
| JP | 7209590 | | 8/1995 |
| JP | 07275200 | | 10/1995 |
| JP | 8024219 | A | 1/1996 |
| JP | 8-50251 | | 2/1996 |
| JP | 08082751 | A | 3/1996 |
| JP | 8114755 | A | 5/1996 |
| JP | 63-66525 | | 3/1998 |
| JP | 10151105 | | 6/1998 |
| JP | 11019026 | | 1/1999 |
| JP | 11-056757 | | 3/1999 |
| JP | 2000131622 | | 5/2000 |
| JP | 2000139821 | | 5/2000 |
| JP | 2000-171727 | | 6/2000 |
| JP | 2000-206422 | | 7/2000 |
| JP | 2001-095751 | | 4/2001 |
| JP | 2001224553 | | 8/2001 |
| JP | 2002-34910 | | 2/2002 |
| JP | 2002-58633 | | 2/2002 |
| JP | 2006198424 | | 3/2006 |
| WO | WO9428783 | | 12/1994 |
| WO | WO9715229 | A1 | 5/1997 |
| WO | WO9732534 | A1 | 9/1997 |
| WO | WO99/23812 | A2 | 11/1998 |
| WO | WO9960916 | | 2/1999 |
| WO | WO0045691 | | 8/2000 |
| WO | WO0049448 | | 8/2000 |
| WO | WO0122741 | A2 | 3/2001 |
| WO | WO0150941 | | 7/2001 |
| WO | WO0165995 | | 9/2001 |
| WO | WO/01/76452 | | 10/2001 |
| WO | WO03013624 | A2 | 2/2003 |
| WO | WO03/098913 | A3 | 5/2003 |

OTHER PUBLICATIONS

Video Camera to "Take"—RF System lab, Dec. 25, 2001; 1 page.
Office action for related Japanese patent application 2003-518624, 5 pages.
European Office Action dated Oct. 21, 2009, for a related European patent application No. 02758761.7; English language; 4 pages.
Israel Office Action dated Nov. 30, 2009, for a related Israel patent application No. 152128; 1 page. EP0928597A2 is submitted herewith.
Japanese Office Action dated Dec. 22, 2009, for a related Japanese Patent Application No. 2004-506277; 11 pages. English translation included.
Office Action from the Patent Office of Canada dated Dec. 29, 2009 for a related Canadian patent application No. 2,456,418, 6 pages.
Office Action dated Dec. 13, 2011 from the Patent Office of Germany in German Patent Application No. 10392670.4; 9 pages.
Japanese Office Action dated Jan. 25, 2011, for a related Japanese Patent Application No. 2004-506277; 9 pages. English translation included.
European Office Action dated Mar. 9, 2011, for related European Patent Application No. 02758761.7-1265; 4 pages total.
Office Action dated Jun. 14, 2010 issued from the United States Patent and Trademark Office for related U.S. Appl. No. 12/166,283; 9 pages.
English translation of Office Action dated Aug. 13, 2010 for related Japanese patent application 2004-506277 derived from PCT/IL2003/000399.
European Patent Office English language Communication pursuant to Article 94(3) EPC for related European patent application No. 01919745.8, dated Oct. 20, 2010, 4 pgs.
Office Action dated Jun. 17, 2011 from the Patent Office of Japan in Japanese Patent Application No. 2004-506277; 5 pages. English translation included.
Japanese Office Action dated May 19, 2011, for Japanese Patent Application No. 2010-278712; 6 pages total. (English translation included).
International Search Report dated Jun. 30, 2004 for related International patent application No. PCTIL0200659, filed Aug. 11, 2002; 1 page.
European Search Report dated Nov. 26, 2008 for related European patent application No. EP02758761, filed Aug. 11, 2002; 6 pages.
Mizuno, K. et al. "New Percutaneous Transluminal Coronary Angioscope" Selected papers on optical fibers in Medicine; SPIE Milestone Series; Bellingham, SPIE, US, vol. MS 11, Jan. 1, 1990 pp. 150-155.
Supplementary European Search Report dated Dec. 22, 2008 for related European patent application No. 02795407.2; 4 pages.
European Examination Report for European Application No. 01919745.8, dated Jul. 20, 2006, 4 pages.
PCT International Search Report dated Oct. 21, 2001, for corresponding PCT International Application No. PCT/IL01/00313, filed Apr. 4, 2001, 3 pages.
PCT International Search Report dated Jul. 9, 2004, for corresponding PCT International Application No. PCT/US03/32975, filed Oct. 17, 2003.
PCT International Search Report dated Jun. 4, 2003, for corresponding PCT International Application No. PCT/IL02/00999, filed Dec. 11, 2002.
Fujipoly America Corp—General Information; http//www.fujipoly.com/general/default.asp; accessed Jun. 11, 2004.
United States Patent and Trademark Office Action dated Aug. 9, 2006 for U.S. Appl. No. 10/759,045, filed Jan. 20, 2004, 9 pages.
"A Review of the Optical Properties of Biological Tissues." Cheong, Prahl and Welch, IEEE Journal of Quantum Electronics, vol. 26, Dec. 12, 1990.
"Optical Properties of Circulating Human Blood in Wavelength Range 400-2500 nm," Andre Rosgan, Journal of Biomedical Optics, Jan. 1999.
Fujipoly America Corp—Zebra Elastomeric Connectors, http://www.fujipoly.com/products/genProductLine.asp?Productline=zebra; accessed Jun. 11, 2004.

European Patent Office English language Examination Report for related European patent application No. 01919745.8, dated Nov. 28, 2007, EPO citing DE19800312, 2 pgs.

Japanese Office Action dated Mar. 18, 2009, for corresponding Japanese patent application No. 2004-506277; English translation; 4 pages.

Office Action dated Dec. 1, 2008 for related Israel Patent Application No. 162420 (in the Hebrew language); 3 pages.

Israel Office Action dated Mar. 24, 2009 for corresponding Israel national phase patent application No. 164962; 2 pages.

* cited by examiner

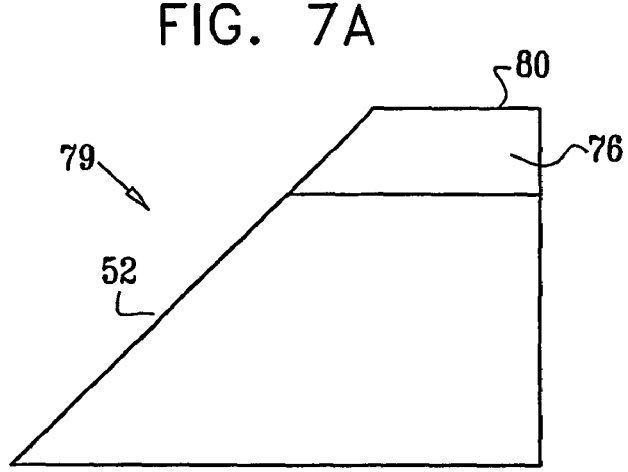
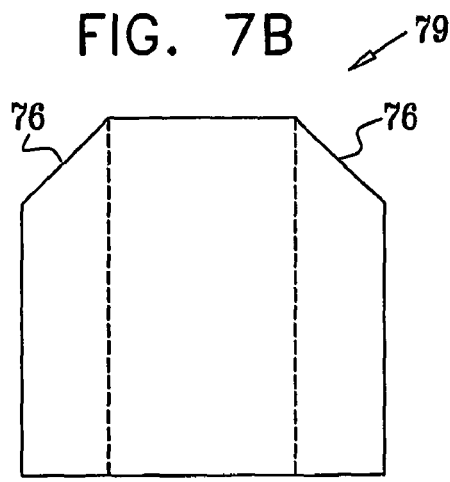
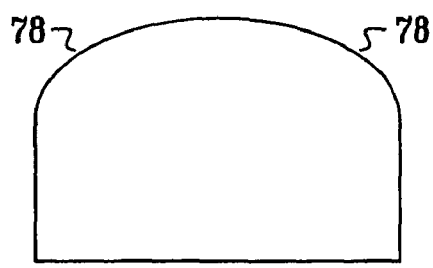
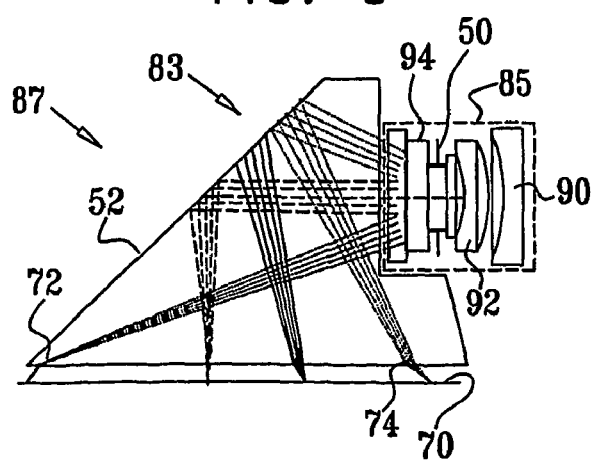

MINIATURE CAMERA HEAD

CROSS-REFERENCE TO RELATED APPLICATIONS

This application claims the benefit of U.S. Provisional Patent Application No. 60/381,478, filed May 16, 2002, whose disclosure is incorporated herein by reference.

FIELD OF THE INVENTION

The present invention relates generally to electronic imaging systems, and particularly to miniature camera heads and associated illumination devices, especially for use in endoscopy.

BACKGROUND OF THE INVENTION

Miniature, remote-head cameras are commonly used in endoscopy and other areas of minimally-invasive surgery. A solid-state imaging sensor is fixed in the distal end of an endoscope, along with suitable imaging optics and an illumination source, in order to capture images within body cavities and passageways. In general it is desirable to reduce the endoscope diameter and at the same time to improve the image quality obtained from the distal-end camera head. These two objectives are often mutually contradictory, since increasing the resolution of the sensor generally requires increasing its size, which leads to increasing the diameter of the endoscope.

A wide variety of distal-end camera heads have been described in the patent literature, based mainly on integration of the sensor, typically a CCD-based sensor, with suitable miniature optics. Some exemplary camera head designs are described in U.S. Pat. Nos. 4,604,992, 4,491,865, 4,746,203, 4,720,178, 5,166,787, 4,803,562, and 5,594,497. Some systems and methods for reducing the overall dimensions of the distal end of an endoscope containing an image sensor are described in U.S. Pat. Nos. 5,929,901, 5,986,693, 6,043,839, 5,376,960, and 4,819,065, and in U.S. Patent Application Publication No. 2001/0031912 A1. One technique that has been suggested for reducing endoscope diameter is to orient the image sensor in a plane that is parallel to the axis of the imaging optics, rather than perpendicular to the plane as in conventional optical designs. Implementations of this technique are described in U.S. Pat. Nos. 4,692,608, 4,646,721 and 4,986,642 and in the above-mentioned U.S. Patent Application Publication 2001/0031912 A1. The disclosures of all the above publications are incorporated herein by reference.

Although most endoscopes provide the user with a single, two-dimensional image, endoscopes with three-dimensional imaging capability are also known in the art. For example, endoscopes that generate stereoscopic images by using two different optical paths are described in U.S. Pat. Nos. 5,944,655, 5,222,477, 4,651,201, 5,191,203, 5,122,650, 5,471,237, 5,673,147, 6,139,490, and 5,603,687, whose disclosures are likewise incorporated herein by reference.

Endoscopes typically use an external illumination source to provide radiation to the distal end of the endoscope via fiber optics. On the other hand, some endoscopes employ illumination devices integrated within the endoscope itself, either at the distal end or at the proximal end of the endoscope. For example, the use of Light Emitting Diodes (LEDs) for this purpose is described in U.S. Pat. Nos. 6,318,887, 6,331,156, 6,260,994, 6,371,907, and 6,340,868, whose disclosures are incorporated herein by reference.

SUMMARY OF THE INVENTION

In embodiments of the present invention, a miniature camera head assembly comprises an objective for collecting optical radiation from an object, and an image sensor, which is oriented in a plane that is substantially non-perpendicular to the optical axis of the objective. Typically, the sensor plane is parallel to the optical axis. A turning mirror, typically a prism, directs the radiation collected by the objective to form a focused image on the image sensor.

The camera head assembly is constructed and configured so as to reduce the radial dimensions of the assembly (measured in a plane perpendicular to the optical axis) to a substantially smaller size than has been achieved in comparable assemblies known in the art. Typically, the assembly is capable of fitting inside a tube, such as the insertion tube of an endoscope, whose diameter is smaller than the diagonal dimension of the image sensor. The reduction of diameter is achieved, inter alia, by a novel optical design, which allows the height of the turning mirror above the image sensor to be reduced in comparison to designs known in the art in which the sensor is oriented parallel to the optical axis. Additionally or alternatively, novel methods for mounting the image sensor chip within the camera head are used to reduce the diameter still further.

Camera head assemblies in accordance with the present invention are thus useful particularly in producing endoscopes of small diameter, relative to endoscopes of comparable resolution that are known in the art. Embodiments of the present invention may additionally be used in other imaging applications in which size and weight are at a premium, such as in military and surveillance cameras and industrial cameras for diagnostics of small cavities.

There is therefore provided, in accordance with an embodiment of the present invention, an electronic imaging device, including:

an optical objective for collecting optical radiation from an object, the objective having an optical axis;

an image sensor, including a matrix of optical detectors arranged in a plane that is substantially non-perpendicular to the optical axis, the image sensor having a lateral dimension in the plane; and a turning mirror, having an optical surface that is positioned so as to reflect the radiation collected by the objective in order to form a focused image in the plane of the image sensor, while a maximum distance from the optical surface to the plane of the image sensor is substantially less than the lateral dimension of the image sensor.

Typically, the maximum distance from the optical surface to the plane of the image sensor is less than approximately 75% of the lateral dimension of the image sensor, and the plane of the image sensor is substantially parallel to the optical axis.

In some embodiments, the turning mirror includes a prism, having an exit face adjacent to the image sensor and an entrance face adjacent to the objective, and the optical surface includes a reflective face of the prism oriented at a diagonal between the entrance and exit faces. In one embodiment, a surface of the prism opposite the exit face is flattened so as to reduce a height of the entrance face of the prism so that the height is substantially less than the lateral dimension of the image sensor, and the flattened surface of the prism has edges that are phased so as to fit the prism within a tube in which the device is contained. Additionally or alternatively, the entrance face of the prism is shaped so as to define an indentation, in which the objective is positioned.

Typically, the image sensor includes a semiconductor chip on which the matrix of optical detectors is formed, wherein the chip is thinned following fabrication of the optical detectors on the chip.

There is also provided, in accordance with an embodiment of the present invention, an electronic imaging device, including:

an optical objective for collecting optical radiation from an object, the objective having an optical axis;

an image sensor oriented in a plane that is substantially non-perpendicular to the optical axis, and including:

a semiconductor chip including a monolithic array of optical detectors and having a predetermined chip area; and a chip package on which the chip is mounted, the package having a total area no greater than about 200% of the chip area; and a turning mirror, having an optical surface that is positioned so as to direct the radiation collected by the objective to form a focused image in the plane of the image sensor.

Preferably, the chip package has a total area no greater than about 150% of the chip area, and more preferably no greater than about 120% of the chip area.

In some embodiments, the device includes an electronic circuit board, on which the image sensor is mounted, wherein the chip package includes a ball grid array (BGA) for contacting the circuit board. In one embodiment, the circuit board is formed so as to define an opening therethrough, and the image sensor is mounted adjacent to the opening, so that the chip package is located on a first side of the circuit board, while the turning mirror is located on a second side of the circuit board, opposite the first side, so as to direct the radiation through the opening onto the image sensor.

There is additionally provided, in accordance with an embodiment of the present invention, an endoscope, including:

an insertion tube of predetermined diameter, the tube having a longitudinal axis and a distal end;

an image sensor fixed within the insertion tube, the image sensor including a matrix of optical detectors arranged in a plane that is substantially non-perpendicular to the longitudinal axis, the image sensor having a diagonal dimension in the plane that is substantially greater than the diameter of the insertion tube; and imaging optics fixed adjacent to the distal end of the tube for focusing optical radiation from an object onto the image sensor so as to form an image of the object on the image sensor.

In one embodiment, the endoscope includes one or more light emitting diodes (LEDs) mounted at the distal end of the insertion tube so as to illuminate the object. The endoscope may also include an electronic circuit board, which includes a first mounting area on which the image sensor is mounted, and a second mounting area on which the one or more LEDs are mounted, wherein the second mounting area is angled relative to the first mounting area.

Alternatively, the endoscope includes a light source located proximally to the distal end of the insertion tube, and a light guide, which passes through the insertion tube so as to emit light from the distal end of the tube to illuminate the object.

There is further provided, in accordance with an embodiment of the present invention, an endoscope, including:

an insertion tube having a longitudinal axis and a distal end; and an electronic imaging device, mounted within the distal end of the insertion tube, and including:

an optical objective for collecting optical radiation from an object, the objective having an optical axis, which is substantially parallel to the longitudinal axis of the insertion tube;

an image sensor, including a matrix of optical detectors arranged in a plane that is substantially non-perpendicular to the optical axis, the image sensor having a lateral dimension in the plane; and a turning mirror, having an optical surface that is positioned so as to reflect the radiation collected by the objective in order to form a focused image in the plane of the image sensor, while a maximum distance from the optical surface to the plane of the image sensor is substantially less than the lateral dimension of the image sensor.

Typically, the turning mirror includes a prism, having an exit face adjacent to the image sensor and an entrance face adjacent to the objective, and the optical surface includes a reflective face of the prism oriented at a diagonal between the entrance and exit faces, wherein a surface of the prism opposite the exit face is flattened and phased so as to fit within the insertion tube.

There is moreover provided, in accordance with an embodiment of the present invention, an endoscope, including:

an insertion tube having a longitudinal axis and a distal end; and an electronic imaging device, mounted within the distal end of the insertion tube, and including:

an optical objective for collecting optical radiation from an object, the objective having an optical axis, which is substantially parallel to the longitudinal axis of the insertion tube;

an image sensor oriented in a plane that is substantially non-perpendicular to the optical axis, and including:

a semiconductor chip including a monolithic array of optical detectors and having a predetermined chip area; and a chip package on which the chip is mounted, the package having a total area no greater than about 200% of the chip area; and a turning mirror, having an optical surface that is positioned so as to direct the radiation collected by the objective to form a focused image in the plane of the image sensor.

There is furthermore provided, in accordance with an embodiment of the present invention, an electronic imaging device, including:

first and second optical objectives for collecting optical radiation from an object, the objectives having respective first and second optical axes, which are mutually substantially parallel;

first and second image sensors, including respective matrices of optical detectors, which are arranged back-to-back in respective first and second planes that are substantially non-perpendicular to the optical axes, the image sensors having a lateral dimension in the respective planes; and first and second turning mirrors, having respective first and second optical surfaces that are positioned so as to reflect the radiation collected by the first and second objectives, respectively, so as to form respective first and second images in the first and second planes of the image sensors, while a maximum distance from the first optical surface to the first plane and from the second optical surface to the second plane is substantially less than the lateral dimension of the image sensors.

Typically, the first and second image sensors are adapted to generate respective first and second electrical signals responsively to the optical radiation that is incident thereon, and the device includes an image processor, which is coupled to receive the first and second electrical signals and to process the signals so as to produce a stereoscopic image of the object.

In a disclosed embodiment, the device includes a circuit board, having first and second sides, wherein the first and second image sensors are mounted respectively on the first and second sides of the circuit board, and the first and second planes are substantially parallel to the optical axis.

There is also provided, in accordance with an embodiment of the present invention, an endoscope, including:

an insertion tube having a longitudinal axis and a distal end; and an electronic imaging device, mounted within the distal end of the insertion tube, and including:

first and second optical objectives for collecting optical radiation from an object, the objectives having respective first and second optical axes, which are mutually substantially parallel;

first and second image sensors, including respective matrices of optical detectors, which are arranged back-to-back in respective first and second planes that are substantially non-perpendicular to the optical axes, the image sensors having a lateral dimension in the respective planes; and first and second turning mirrors, having respective first and second optical surfaces that are positioned so as to reflect the radiation collected by the first and second objectives, respectively, so as to form respective first and second images in the first and second planes of the image sensors, while a maximum distance from the first optical surface to the first plane and from the second optical surface to the second plane is substantially less than the lateral dimension of the image sensors.

There is further provided, in accordance with an embodiment of the present invention, imaging apparatus, including:

a camera head including an image sensor, which is adapted to capture an electronic image of an object; and a light source, which includes:

an array of light emitting diode (LEDs), which are adapted to generate optical radiation;

an array of optical fibers, having respective proximal and distal ends, wherein the proximal ends are respectively coupled to the LEDs so that each of the fibers receives the radiation emitted by a respective one of the LEDs, and the distal ends are arranged to convey the radiation to a vicinity of the camera head so as to illuminate the object; and a controller, which is adapted to drive the LEDs to emit the optical radiation at different, respective intensities so as to adjust illumination of the object.

Typically, the controller is adapted to drive the LEDs responsively to the image of the object, so as to adjust for uneven brightness in the image.

There is moreover provided, in accordance with an embodiment of the present invention, a method for electronic imaging, including:

aligning an optical objective to collect optical radiation from an object along an optical axis;

arranging an image sensor, including a matrix of optical detectors, in a plane that is substantially non-perpendicular to the optical axis, the image sensor having a lateral dimension in the plane; and positioning an optical surface of a turning mirror so as to reflect the radiation collected by the objective in order to form a focused image in the plane of the image sensor, such that a maximum distance from the optical surface to the plane of the image sensor is substantially less than the lateral dimension of the image sensor.

There is furthermore provided, in accordance with an embodiment of the present invention, a method for electronic imaging, including:

aligning an optical objective for collecting optical radiation from an object along an optical axis;

orienting an image sensor in a plane that is substantially non-perpendicular to the optical axis, the image sensor including a semiconductor chip, which includes a monolithic array of optical detectors and having a predetermined chip area and is mounted on a chip package having a total area no greater than about 200% of the chip area; and positioning an optical surface of a turning mirror so as to direct the radiation collected by the objective to form a focused image in the plane of the image sensor.

There is moreover provided, in accordance with an embodiment of the present invention, a method for endoscopic imaging, including:

providing an insertion tube of predetermined diameter, the tube having a longitudinal axis and a distal end;

fixing an image sensor within the insertion tube, the image sensor including a matrix of optical detectors arranged in a plane that is substantially non-perpendicular to the longitudinal axis, the image sensor having a diagonal dimension in the plane that is substantially greater than the diameter of the insertion tube; and aligning imaging optics adjacent to the distal end of the tube, so as to focus optical radiation from an object onto the image sensor in order to form an image of the object on the image sensor.

The present invention will be more fully understood from the following detailed description of the embodiments thereof, taken together with the drawings in which:

BRIEF DESCRIPTION OF THE DRAWINGS

FIGS. 7A and 7B are schematic side and end views, respectively, of a prism for use in a camera head assembly, in accordance with an embodiment of the present invention;

FIG. 8 is a schematic end view of a prism for use in a camera head assembly, in accordance with an alternative embodiment of the present invention;

FIG. 9 is a schematic optical ray diagram showing elements of a camera head assembly, in accordance with another embodiment of the present invention;

DETAILED DESCRIPTION OF EMBODIMENTS

Figure 1:
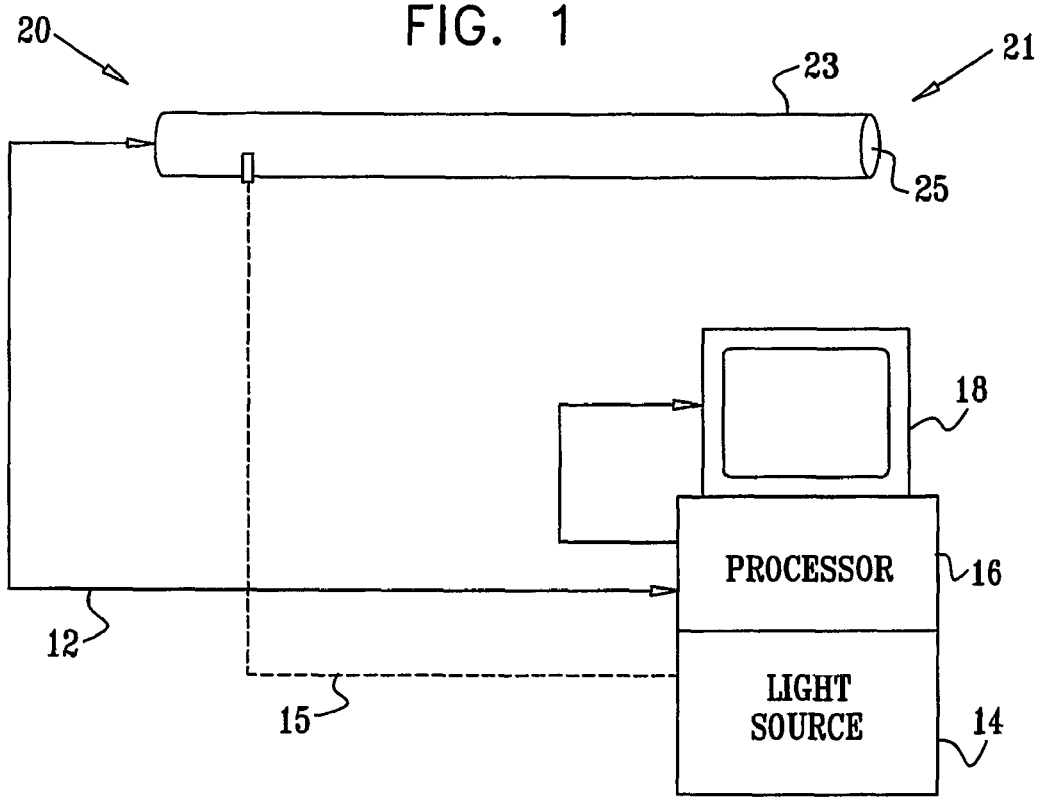
FIG. 1 is a block diagram that schematically illustrates an endoscopic imaging system, in accordance with an embodiment of the present invention.

Reference is now made to FIG. 1, which is a block diagram that schematically illustrates an endoscopic imaging system 20, in accordance with an embodiment of the present invention. System 20 comprises an endoscope 21, which is connected by a cable 12 to a processing unit 16. The endoscope comprises an insertion tube 23, containing a miniature camera head at its distal end 25, as shown and described hereinbelow. Typically, the endoscope also contains an internal light source, for illuminating the area adjacent to the distal end of the endoscope, which is imaged by the camera head. Alternatively or additionally, an external light source 14 may be used to provide illumination via a fiberoptic bundle 15 to a light guide within endoscope 21. The external light source may alternatively be coupled optically to the distal end of the endoscope via one or more liquid-filled light guides. Light source 14 typically comprises one or more solid-state emitters, such as LEDs, as described below. Alternatively, the light source may comprise a gas discharge lamp, as is known in the art.

A processing unit 16 receives signals from the miniature camera head via cable 12, and processes the signals to generate video images on a display 18. Processing unit 16 may be either a stand-alone unit with image processing capabilities and control circuitry, or a personal computer (PC) with suitable front-end circuits and software. Alternatively, the functions of the processing unit may be performed by electronics within endoscope 21. The electronics, as well as a light source for providing illumination at distal end 25, may be contained within a handle (not shown) that is used in manipulating the endoscope. In some embodiments, as illustrated below in FIGS. 15 and 16, endoscope 20 provides stereoscopic image information, and the processing unit may perform three-dimensional image reconstruction and display. Processing unit 16 may further function as a controller for light source 14, as is further described below.

Figure 2:
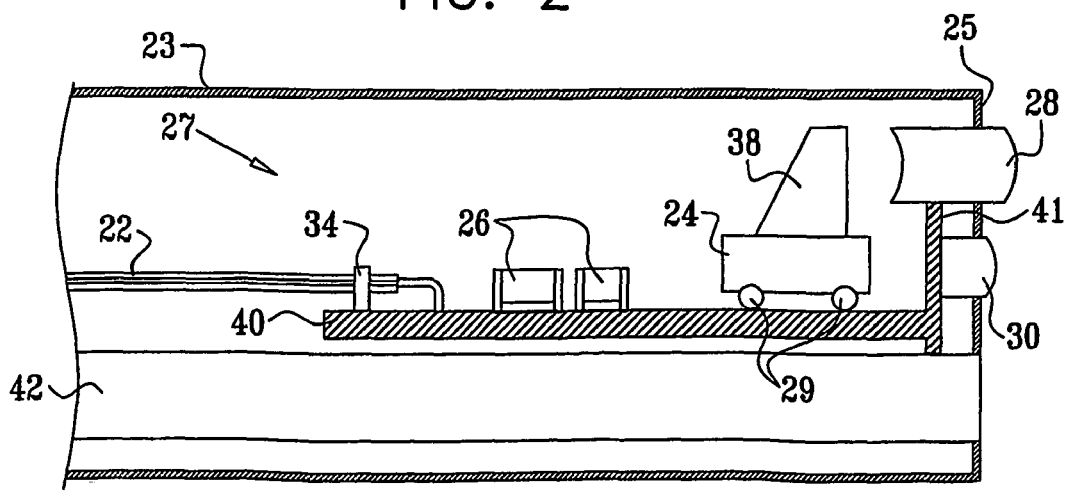
FIGS. 2 and 3 are schematic, sectional diagrams of camera head assemblies, in accordance with embodiments of the present invention.

FIG. 2 is a schematic, sectional illustration showing a miniature camera head assembly 27 within insertion tube 23, in accordance with an embodiment of the present invention. One or more light sources 30 illuminate the region immediately distal to endoscope 21. Typically, light sources 30 comprise white-light LEDs, but alternatively, miniature light source of different types may be used, including LEDs of other colors or infrared LEDs or, in some applications, a miniature incandescent source, as is known in the art.

An optical objective 28, mounted at distal end 25, collects and focuses light from objects illuminated by light source 30. A turning mirror, typically comprising a right angle prism 38, reflects the light collected by objective 28 to focus on the focal plane of an image sensor 24. Sensor 24 typically comprises a two-dimensional matrix of detector elements, based on CMOS, CCD or other solid-state imaging technology, as is known in the art. For example, sensor 24 may comprise a MI0133 CMOS imaging array, produced by Micron Technology Inc., of Boise, Id., comprising 377×312 detector elements, giving an imaging area of about 2×1.8 mm, out of overall chip dimensions of 3×3.7 mm (with a diagonal dimension of about 4.8 mm). Typically, prism 38 is arranged to turn the optical axis of the focused rays by 90°, so that the focal plane of the sensor is substantially parallel to the optical axis of objective 28. Alternatively, the turning mirror and image sensor may be arranged so that the sensor is oriented at a different angle, non-perpendicular to the optical axis of the objective.

Sensor 24 is mounted on a circuit substrate, such as a printed circuit board 40, by balls 29, which are arranged in a ball grid array (BGA), as is known in the art. This method of packaging and mounting sensor 24 enables the sensor to be contained in a chip-scale package, which is not much wider than the sensor chip itself. This and other methods of chip-scale packaging and mounting of the sensor chip are described in detail hereinbelow. A cable 22 passing through endoscope 21 connects assembly 27 to processing unit 16. One or more controller and communication interface chips 26 on board 40 serve to pass electrical signals from image sensor 24 to processing unit 16 and to receive control inputs from the processing unit. Cable 22 is typically mechanically secured to board 40 by a cable clamp 34. A perpendicular extension 41 of board 40 may be provided for mounting light sources 30. Alternatively, board 40 may comprise a flexible end portion, which is bent to mount light sources 30. Further alternatively, any other suitable means known in the art may be used to mount the light sources at distal end 25. A working channel 42, which runs substantially the entire length of endoscope 21, is located beneath board 40.

Figure 3:
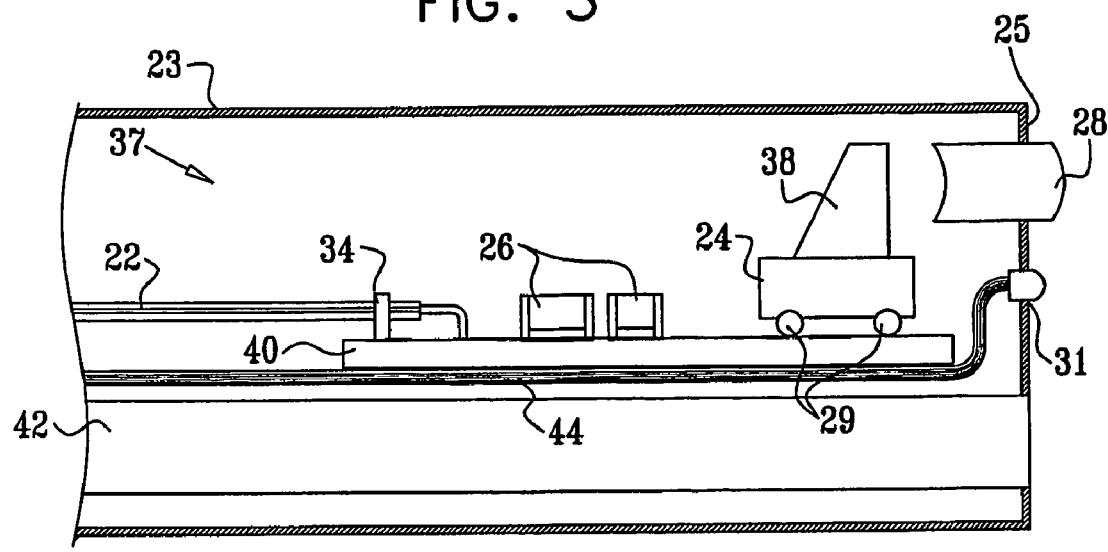

FIG. 3 is a schematic, sectional illustration of a miniature camera head assembly 37, in accordance with another embodiment of the present invention. Assembly 37 is similar to assembly 27, shown in FIG. 2, except that in the assembly 37, a remote light source is used to provide illumination to distal end 25 via a fiberoptic light guide 44 running the length of endoscope 21. The remote light source may comprise external light source 14 or an internal light source (not shown) located proximally within endoscope 21. An illumination lens 31 directs the light from light guide 44 onto objects distal to the endoscope, in place of light source 30. Light guide 44 typically comprises multiple optical fibers, which may branch at distal end 25 in order to output light through multiple illumination lenses. As a further alternative, one or more distal-end light sources 30, as shown in FIG. 2, may be used in combination with one or more lenses 31, fed by light guide 44.

Figure 4:
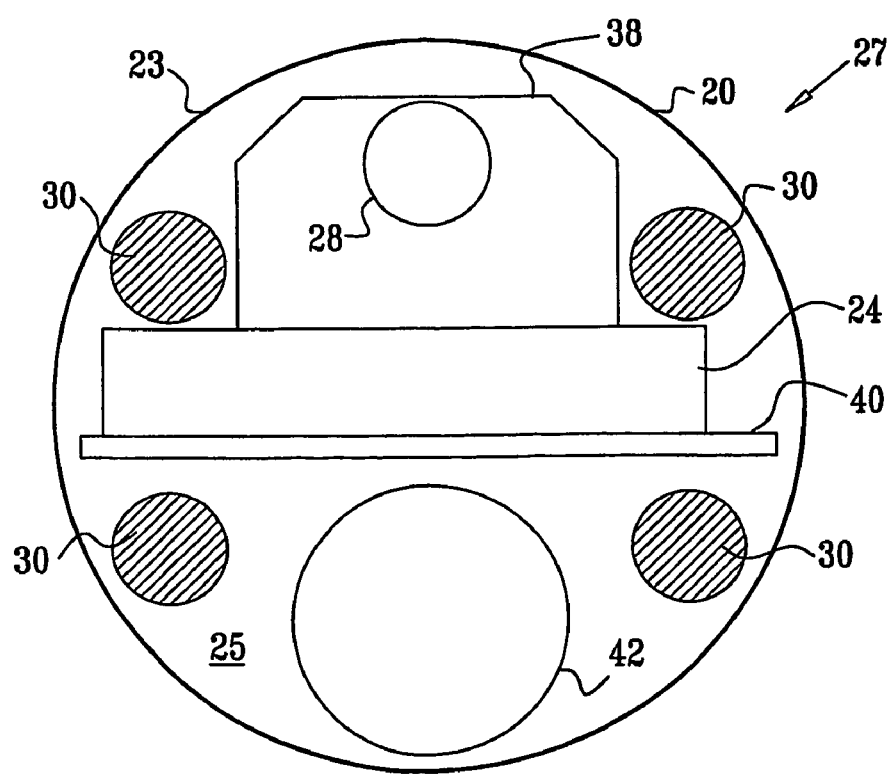
FIG. 4 is a schematic end view of the camera head assembly of FIG. 2.

FIG. 4 is a schematic end view of insertion tube 23, illustrating the elements of assembly 27 (FIG. 2) at distal end 25. Four light sources 30 are shown in the present embodiment, but more or fewer illumination sources may be employed as necessary to provide adequate illumination. Assembly 37 may be similarly configured, using illumination lenses 31 in place of light sources 30. It will be observed that the minimum achievable diameter of insertion tube 23 is determined approximately by the lateral (width) dimensions of sensor 24 and board 40 and by the height of prism 38 above the plane of sensor 24. Techniques and optical designs for reducing the height of prism 38 are described hereinbelow. Preferably, the chip on which sensor 24 is fabricated is thinned, and the chip package (if used) and board 40 are designed so that the board is not much wider than the chip itself. In this manner, the diameter of tube 23 may be made smaller than the diagonal dimension of sensor 24.

Minimizing the overall radial dimensions of assemblies 27 and 37 is a major consideration in their design, so that insertion tube 23 may itself be made narrower and pass more easily through narrow body passages. As noted above, typical lateral dimensions for image sensor 24 are 3×3.7 mm. The sensor chip as fabricated is typically about 0.7 mm thick. Board 40 has a typical thickness of 0.3 mm. Tube 23 has a wall thickness of about 0.15 mm. In the view shown in FIG. 4, it can be seen that the diameter of tube 23 is limited in the horizontal direction by the width of board 40 plus twice the wall thickness of the insertion tube. Taking the board width to be 3 mm, the minimal diameter in the horizontal direction is given by:

$$\text{diameter} \geq 3 + 2 \cdot 0.15 = 3.3 \text{ mm} \tag{1}$$

In the vertical direction, on the other hand, the minimal diameter of tube 23 is limited by the thickness of board 40, plus twice the thickness of sensor 24 and twice the prism height (assuming board 40 to be roughly centered within tube 23), plus twice the thickness of the insertion tube. In conventional optical designs, the height of the prism (or other turning mirror) can be no less than the lateral dimension of the sensor array, i.e., 2 mm in the present example. The limit of the diameter in the vertical direction is then:

$$\text{diameter} \geq 0.3 + 2 \cdot (0.7 + 2 + 0.15) = 6.0 \text{ mm} \tag{2}$$

In embodiments of the present invention, however, the prism height is reduced, as shown in FIG. 4, so that the limiting diameter of insertion tube 23 in the vertical direction is substantially reduced as well. The sensor chip may be thinned, as well, below the 0.7 mm standard thickness. As a result of these steps, the minimal diameter of tube 23 is reduced, preferably to less than the diagonal dimension of sensor 24 (4.8 mm in the present example).

Figure 5:
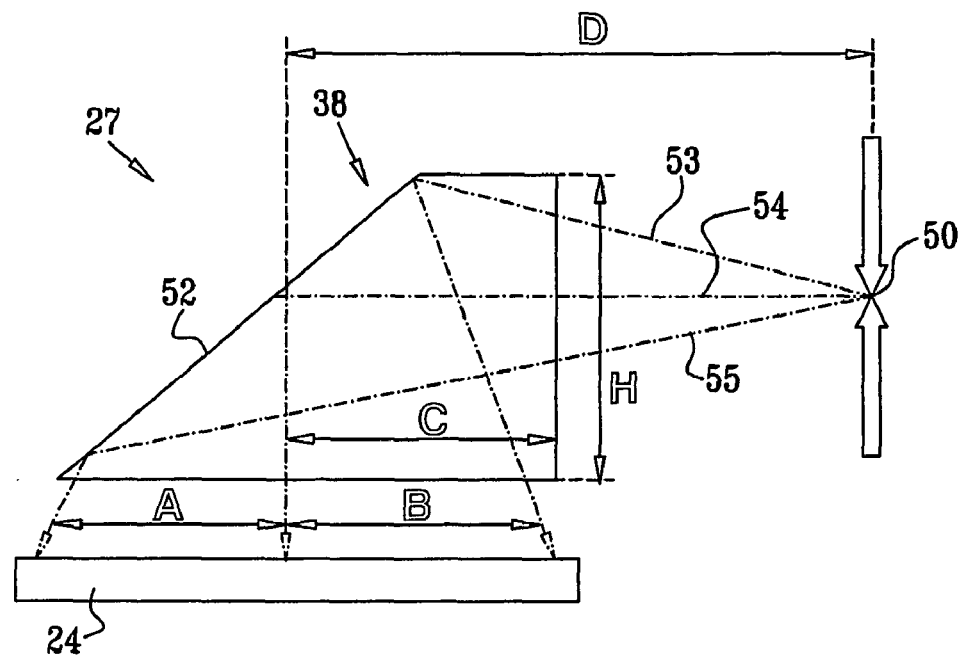
FIG. 5 is schematic optical ray diagram of a prism used in a camera head assembly, in accordance with an embodiment of the present invention.

Reference is now made to FIG. 5, which is a simplified ray diagram of prism 38, showing how a minimal height H of the prism is determined, in accordance with an embodiment of the present invention. A central ray 54 and extreme rays 53 and 55 emanate from an aperture stop 50 of optical assembly 27 and are reflected at a reflecting surface 52 of prism 38 to focus on sensor 24. Ray 54 is incident at the center of sensor 24, while rays 53 and 55 correspond to the edges of the image. Let D be the distance from stop 50 to the point at which ray 54 reflects from surface 52, and let A be the horizontal distance between the points at which rays 54 and 55 impinge on sensor 24. (In other words, A should be roughly half the width of the active area of sensor 24, so that $A = Y\frac{1}{2}$ mm = 1 mm in the present example.) The relationship between the height H of prism 38 and the distances A and D can be expressed as:

$$H = 2A \cdot (A+D)/(2A+D) \tag{3}$$

Thus, reducing D for a given value of A allows the height H of prism 38 to be reduced. Let C be defined as the horizontal distance between the front surface of prism 38 and the point at which ray 54 reflects from surface 52, while B is defined as the horizontal distance between the points at which rays 54 and 53 impinge on sensor 24. Assuming the distances C and B to be roughly equal, as shown in FIG. 5, and B to be roughly equal to A, the minimal distance, $D_{min}$, is:

$$D_{min} = B = C \tag{4}$$

which gives:

$$H_{min} = 1.33 \cdot A \tag{5}$$

Inserting the value H=1.33 mm into equation (2) gives 4.66 mm as the limiting diameter of tube 23. It will be observed that this limit is less than the diagonal dimension of sensor 24, which is about 4.8 mm, as noted above.

In practical optical designs, it may be difficult to reduce D to the $D_{min}$ value given by equation (4), because this constraint would appear to require that aperture stop 50 be located at the entrance face of prism 38. Even at a larger value of D, however, it is still possible, based on the present invention, to reduce H substantially below the nominal height of $H \approx 2A$ that is typical of turning mirrors known in the art (i.e., equal height and base dimensions of the prism, with the base dimension roughly equal to the lateral dimension of the image sensor). For example, for D=2A, a prism of height H=1.5*A may be used, so that the height of the prism is approximately 75% or less of the lateral dimension of sensor 24. As shown below in FIG. 9, it is also possible to design the turning prism so that C<B, whereby H can be reduced still further, down to a limit of $H_{min} \approx A$.

Figure 6:
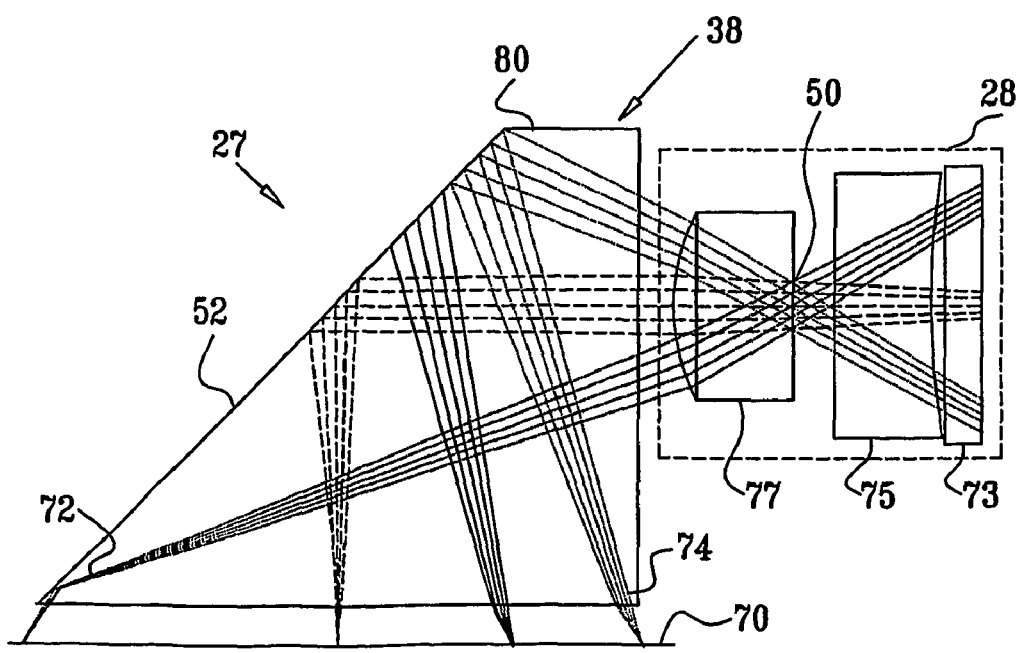
FIG. 6 is a schematic optical ray diagram showing elements of a camera head assembly, in accordance with an embodiment of the present invention.

FIG. 6 is a ray diagram showing an exemplary optical design of assembly 27, in accordance with an embodiment of the present invention. Light ray groups 72 and 74 define the edges of an image collected by objective 28 and reflected by surface 52 onto a focal plane 70 of sensor 24. Prism 38 is designed so that ray group 72 exits from the prism at its lower left corner, while ray group 74 exits from the prism at its lower right corner. The prism is truncated in a plane 80 at a height that is slightly greater than 1.33*A. Because of the short distance D between aperture stop 50 and surface 52, the upper portion of the surface (above plane 80) is not required and can be eliminated in the manner shown in this figure.

Objective 28 in this embodiment comprises a protective window 73, followed by two lenses 75 and 77, with air gaps between them. Prism 38 and both lenses are made from PMMA. Aperture stop 50 is located at the first surface of lens 77. The front focal length of objective 28 is 10 mm in water. Table I below lists the optical parameters of this design:

TABLE I

EXEMPLARY OPTICAL DESIGN PARAMETERS OF FIG. 6

Protective window 73 made from BK7 with thickness 0.1 mm.
Air gap from protective window to first surface of lens 75: 0.05 mm.
Radius of curvature of first surface of lens 75: −.7982 (concave surface).
Thickness of lens 75: 0.3 mm.
Radius of curvature of second surface of lens 75: 1.593 (concave surface).
Air distance between second surface of lens 75 and aperture stop 50: 0.157 mm.
Aperture stop diameter: 0.29 mm.
Air distance between aperture stop 50 and first surface of lens 77: 0.
Radius of curvature of first surface of lens 77: 1.756 (convex surface).
Thickness of lens 77: 0.4 mm.
Radius of curvature of second surface of lens 77: −0.547 (convex surface)
Air distance between second surface of lens 77 and prism 38: 0.1 mm.
45° prism, base 2 mm × 2 mm.
Distance between exit surface of prism and sensor 24: 0.15 mm.

Reference is now made to FIGS. 7A and 7B, which are schematic side and end views, respectively, of a prism 39 with further reduced dimensions in accordance with an embodiment of the present invention. Side phases 76 are cut on either side of plane 80, so as to allow the prism to be more easily integrated into a round tube, as shown in FIG. 4. The side phases do not affect the optical performance of prism 39, since they involve removal of material only from areas of surface 52 that are not used in reflecting the image rays from objective 28 to sensor 24.

FIG. 8 is a schematic end view of another prism 81, having rounded phases 78, in accordance with an alternative embodiment of the present invention. Alternatively or additionally, any number of straight side phases may be employed to yield a prism with a shape ranging from that shown in FIGS. 7A and 7B to that shown in FIG. 8.

FIG. 9 is a ray diagram showing an exemplary optical design of another camera head assembly 87, in accordance with a further embodiment of the present invention. In this embodiment, a prism 83 and an accompanying objective 85 are designed so that the height of the prism is reduced even more than in the preceding embodiment. For this purpose, objective 85 (and hence aperture stop 50) is placed closer to surface 52, by means of an indentation formed in the entrance surface of prism 83. Equivalently, a front extension may added to the prism. In either case, the lower right portion of the prism serves to prevent deformation of ray group 74.

Objective 85 in this embodiment comprises three lenses 90, 92 and 94, of which lenses 92 and 94 are doublets, with air gaps between the lenses. Aperture stop 50 is located between lenses 92 and 94. The front focal length of objective 28 is 30 mm in water. Table II below lists the optical parameters of this design:

TABLE II

EXEMPLARY OPTICAL DESIGN PARAMETERS OF FIG. 9

Lens 90 made from SK16 with thickness 0.1 mm.
First radius of curvature of lens 90 is infinity (flat), second is 0.927 (concave).
Air gap from lens 90 to first surface of lens 92: 0.05 mm.
Lens 92 made from SK16/SFL6.
Radius of curvature of first surface of lens 92: 0.461 (convex surface).
Radius of curvature of second surface of lens 92: 0.4135 (concave to first element and convex to cemented element).
Radius of curvature of third surface of lens 92: 1.111 (concave surface).
Thicknesses of lens 92: 0.1/0.1 mm (overall doublet thickness 0.2 mm).
Air distance between third surface of lens 92 and aperture stop 50: 0.05 mm.
Air distance between aperture stop 50 and first surface of lens 94: 0.05 mm.
Lens 94 made from SFL6/SK16.
Radius of curvature of first surface of lens 94: 2.376 (convex surface).
Radius of curvature of second surface of lens 94: 7.4557 (concave to first element and convex to cemented element).
Radius of curvature of third surface of lens 94: 19.037 (concave surface).
Thicknesses of lens 94: 0.1/0.1 mm (overall doublet thickness 0.2 mm).
Air distance between third surface of lens 94 and prism 83: 0.05 mm.
45° prism, 1.7 mm × 1.7 mm base, made from SFL6.
Distance between exit surface of prism and focal plane 70: 0.05 mm.

Figure 10:
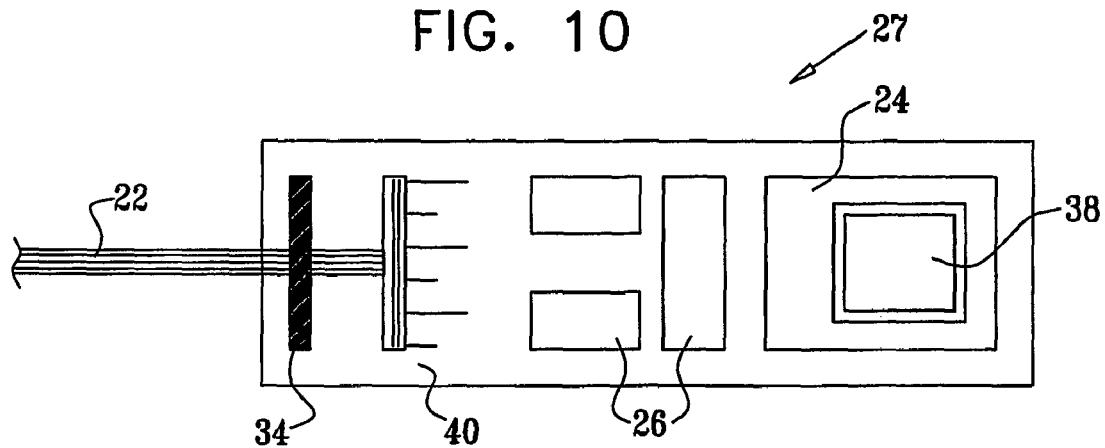
FIG. 10 is a schematic top view of a sensor assembly used in a camera head, in accordance with an embodiment of the present invention.

Reference is now made to FIG. 10, which is a schematic top view of the sensor assembly portion of camera head assembly 27, which was shown in sectional view in FIG. 2. In this embodiment, image sensor 24 is contained in a ShellOP package, which is produced by ShellCase Ltd., of Jerusalem, Israel, or in another, similar type of package. The input/output (I/O) pads of the image sensor chip are extended to the bottom of the die by extension wires (not shown), where they are connected to board 40 by balls 29, as noted above. This technology is one implementation of Ball Grid Array (BGA) packaging technology, as is known in the art. Before packaging the sensor chip in the ShellOP package, the silicon die is thinned, so that the total thickness of the chip plus package is typically about 0.7 mm. The limiting diameter of insertion tube 23, as given by equation (2), is maintained accordingly.

Note also that the total area of sensor 24 plus its package, as measured in the plane of FIG. 10, is only slightly greater than the area of the sensor chip itself. Therefore, the limiting diameter of the insertion tube in the horizontal direction, as given by equation (1), is not substantially increased by the chip package. Preferably, in this and the other embodiments described below, sensor 24 is contained in a chip-scale package that is, in terms of total area in the plane of the sensor, no more than 200% of the area of the sensor chip itself. More preferably, the total area of the chip-scale package is not more than 150% of the area of the sensor chip, and most preferably, not more than about 120%. It will be understood that these dimensions are approximate, and may be varied by ±25% while still realizing this aspect of the present invention.

Similarly, board 40 is preferably only minimally wider than the package of sensor 24 (wherein the width dimension in this case is taken in the vertical direction in FIG. 10, or equivalently, the horizontal direction in FIG. 4). In order to minimize the required width of the board, sensor 24 may be produced with I/O pads on only two sides of the chip, typically on the left and right sides in the view shown in FIG. 10.

Figure 11:
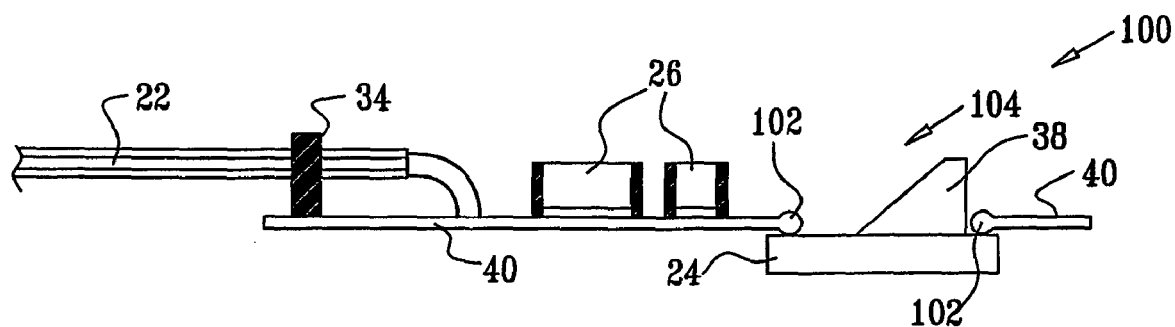
FIG. 11 is a schematic sectional view of a sensor assembly used in a camera head, in accordance with an embodiment of the present invention.

FIG. 11 is a schematic sectional view of a sensor assembly 100 used in a camera head, in accordance with another embodiment of the present invention. In this embodiment, image sensor 24 is contained in another type of BGA package, such as a flip-chip package, as is known in the art, or a package of the type produced by ShellCase. The sensor is mounted below a "window" 104 in board 40, and the sensor I/O pads (not shown) are connected to PCB 40 by balls 102. This method of BGA packaging of image sensor 24 similarly includes a step of thinning the silicon die, to yield a typical overall chip package thickness of 0.4 mm. This mounting scheme, with sensor 24 mounted below board and prism 38 protruding above it, is useful in further reducing the diameter limit imposed by equation (2).

Figure 12:
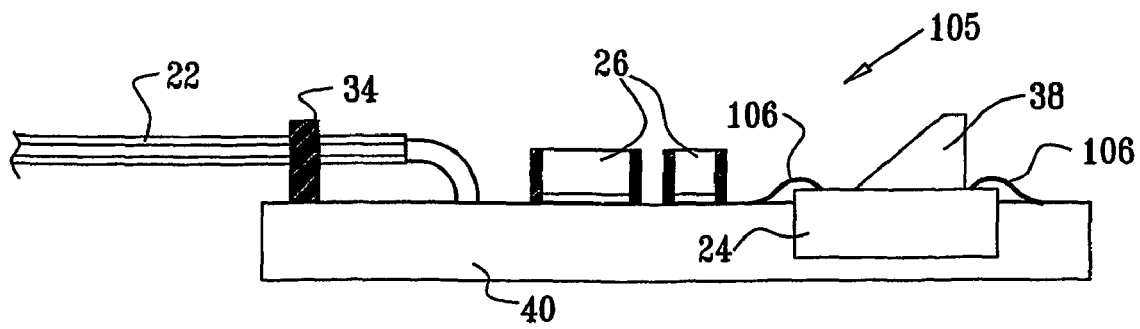
FIG. 12 is a schematic sectional view of a sensor assembly used in a camera head, in accordance with another embodiment of the present invention.

FIG. 12 is a schematic sectional view of a sensor assembly 105 used in a camera head, in accordance with still another embodiment of the present invention. In this embodiment, image sensor 24 is fitted into a recess in board 40, which is made to fit the sensor chip. The sensor is electrically coupled to board 40 by bonding wires 106, as is known in the art. As in the preceding embodiments, the sensor chip is preferably thinned before assembly into board 40. The chip may be fitted into the recess in board 40 as a bare chip without further packaging. Alternatively, the bare chip may be mounted directly on the surface of board 40, without a special recess.

Figure 13:
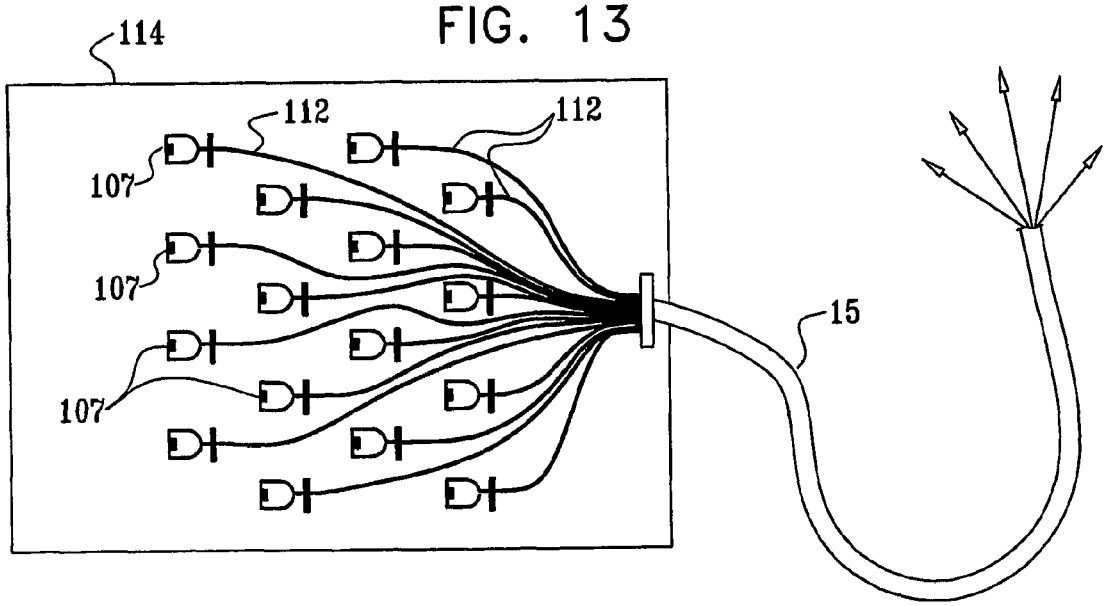
FIG. 13 is a schematic top view of a illumination assembly for use in an endoscopy system, in accordance with an embodiment of the present invention.

FIG. 13 is a schematic top view of an array 114 of LEDs 107, each coupled to a respective light guide 112, in accordance with an embodiment of the present invention. The light guides are joined into bundle 15, which feeds light to endoscope 21. LEDs 107 may be individually controlled, in order to compensate for uneven illumination intensity within the field of view of sensor 24 at the distal end of endoscope 21, as described, for example, in the above-mentioned U.S. Patent Application Publication 2001/0031912 A1. LEDs 107 may all emit the same color light, such as white light, or alternatively, different LEDs may be configured to emit different colors, include infrared light.

Figure 14:
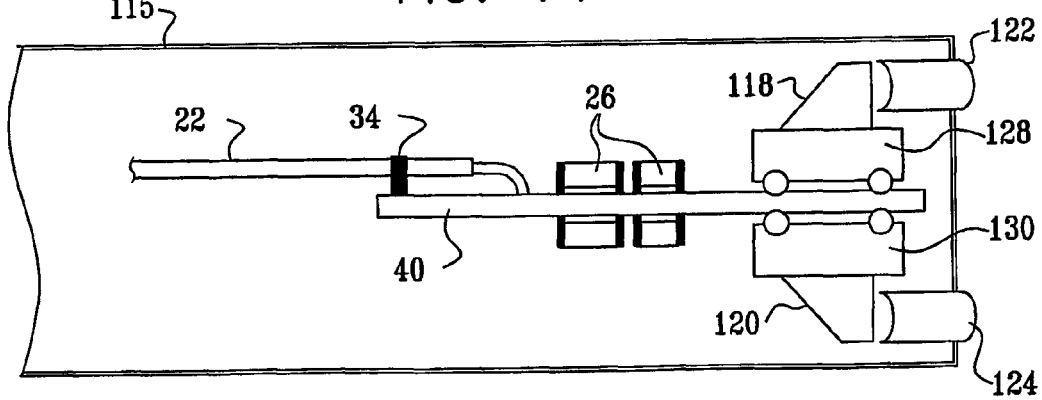
FIGS. 14 and 15 are a schematic sectional side view and an end view, respectively, of a stereoscopic camera head assembly, in accordance with an embodiment of the present invention.
Figure 15:
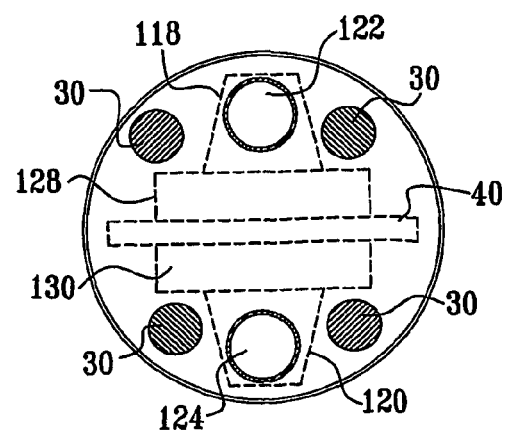

FIGS. 14 and 15 schematically illustrate a miniature camera head assembly 115 for stereoscopic imaging, in accordance with an embodiment of the present invention. FIG. 14 is a sectional side view of assembly 115, while FIG. 15 is an end view, seen from the right side of FIG. 14. The design of assembly 115 is based on the principles of assembly 27, as described above in detail, and is thus suitable for use within the distal end of an endoscope. Two image sensors 128 and 130 in assembly 115 are mounted back-to-back, on opposite sides of board 40. BGA mounting may be used for this purpose, for example, as described above. Each sensor has a respective turning prism 118, 120 and an objective 122, 124. Thus, image sensors 128 and 130 capture images of objects in the field of view of objectives 122 and 124, along optical axes that are parallel but mutually displaced. Processor 16 (FIG. 1) receives the signals generated by the image sensors, and processes the signals to produce pseudo-three-dimensional pictures on display 18. Based on the design principles described above, including minimizing the heights of prisms 118 and 120 and reducing the width and thickness of sensors 128 and 130, the overall radial diameter of assembly 115 can be made substantially smaller than that of miniature stereoscopic camera heads that are known in the art for producing images of comparable resolution.

Although the embodiments described above are directed particularly to endoscopic imaging, the principles of the present invention may similarly be applied in other areas of electronic imaging in which size and weight are at a premium, such as in military and surveillance cameras and industrial cameras for diagnostics of small cavities. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An electronic imaging device, comprising:
    an optical objective for collecting optical radiation from an object, the objective having an optical axis;
    an image sensor, comprising a planar matrix of optical detectors arranged in a plane that is substantially parallel to the optical axis, the image sensor having an active area, which has a lateral dimension in the plane;
    a prism, having an exit face adjacent to the image sensor and an entrance face adjacent to the objective, and an optical surface comprising a reflective face of the prism, wherein the optical surface is positioned so as to reflect the radiation collected by the objective in order to form a focused image in the plane of the image sensor, while a maximum distance among distances from points on the optical surface to the plane of the image sensor is substantially less than the lateral dimension of the active area of the image sensor;
    an aperture stop placed in front of the entrance face; and
    wherein a surface of the prism opposite the exit face is flattened parallel to the exit face so as to reduce a height of the entrance face of the prism, and the aperture stop is placed close to the entrance face so that the height is substantially less than the lateral dimension of the active area of the image sensor.

2. The device according to claim 1, wherein the maximum distance from the optical surface to the plane of the image sensor is less than approximately 75% of the lateral dimension of the image sensor.

3. The device according to claim 1, wherein the flattened surface of the prism has edges that are phased so as to fit the prism within a tube in which the device is contained.

4. The device according to claim 1, wherein the entrance face of the prism is shaped so as to define an indentation, in which the objective is positioned.

5. The device according to claim 1, wherein the image sensor comprises:
    a semiconductor chip on which the matrix of optical detectors is formed, the chip having a chip area determined by the lateral dimensions of the image sensor; and
    a chip package on which the chip is mounted, the package having a total area no greater than 200% of the chip area.

6. The device according to claim 1, wherein the image sensor comprises a semiconductor chip on which the matrix of optical detectors is formed, wherein the chip is thinned following fabrication of the optical detectors on the chip.

7. The device according to claim 1, wherein the image sensor comprises a semiconductor chip on which the matrix of optical detectors is formed, the chip having a diagonal dimension that is determined by the lateral dimension of the image sensor, and wherein the objective, prism and image sensor are designed and assembled so that the device can be contained within a tube having a diameter no greater than the diagonal dimension of the chip.

8. An electronic imaging device, comprising:
    an optical objective for collecting optical radiation from an object, the objective having an optical axis;
    an image sensor oriented in a plane that is substantially parallel to the optical axis, and comprising:
        a semiconductor chip comprising a planar monolithic array of optical detectors having an active area, which has a lateral dimension in the plane of the image sensor, and having a predetermined chip area; and
        a chip package on which the chip is mounted, the package having a total area no greater than about 200% of the chip area; and
    a prism, having an exit face adjacent to the image sensor and an entrance face adjacent to the objective, and an optical surface comprising a reflective face of the prism, wherein the optical surface is positioned so as to direct the radiation collected by the objective to form a focused image in the plane of the image sensor, while a maximum distance among distances from points on the optical surface to the plane of the image sensor is substantially less that the lateral dimension of the active area of the array of optical detectors;
    an aperture stop placed in front of the entrance face; and
    wherein a surface of the prism opposite the exit face is flattened parallel to the exit face so as to reduce a height of the entrance face of the prism, and the aperture stop is placed close to the entrance face so that the height is substantially less than the lateral dimension of the active area of the array of optical detectors.

9. The device according to claim 8, wherein the chip package has a total area no greater than about 150% of the chip area.

10. The device according to claim 9, wherein the chip package has a total area no greater than about 120% of the chip area.

11. The device according to claim 8, wherein the semiconductor chip is thinned following fabrication of the optical detectors on the chip.

12. The device according to claim 8, wherein the semiconductor chip has a diagonal dimension corresponding to the chip area, and wherein the objective, prism and image sensor are designed and assembled so that the device can be contained within a tube having a diameter no greater than the diagonal dimension of the chip.

13. The device according to claim 8, and comprising an electronic circuit board, on which the image sensor is mounted, wherein the chip package comprises a ball grid array (BGA) for contacting the circuit board.

14. The device according to claim 13, wherein the circuit board is formed so as to define an opening therethrough, and wherein the image sensor is mounted adjacent to the opening, so that the chip package is located on a first side of the circuit board, while the prism is located on a second side of the circuit board, opposite the first side, so as to direct the radiation through the opening onto the image sensor.

15. An endoscope, comprising:
    an insertion tube of predetermined diameter, the tube having a longitudinal axis and a distal end;
    an image sensor fixed within the insertion tube, the image sensor comprising a planar matrix of optical detectors arranged in a plane that is substantially parallel to the longitudinal axis, the image sensor having an active area, which has a lateral dimension in the plane, and having a diagonal dimension in the plane that is substantially greater than the diameter of the insertion tube; and
    imaging optics fixed adjacent to the distal end of the tube for focusing optical radiation from an object onto the image sensor so as to form an image of the object on the image sensor, and wherein the imaging optics comprise:
- an optical objective for collecting the optical radiation from the object;
- a prism, having an exit face adjacent to the image sensor and an entrance face adjacent to the objective, and an optical surface comprising a reflective face of the prism, wherein the optical surface is positioned so as to reflect the radiation collected by the objective in order to form a focused image in the plane of the image sensor, while a maximum distance among distances from points on the optical surface to the plane of the image sensor is substantially less than the lateral dimension of the active area of the image sensor;
- an aperture stop placed in front of the entrance face; and
- wherein a surface of the prism opposite the exit face is flattened parallel to the exit face so as to reduce a height of the entrance face of the prism, and the aperture stop is placed close to the entrance face so that the height is substantially less than the lateral dimension of the active area of the image sensor.

16. The endoscope according to claim 15, wherein the image sensor comprises:
- a semiconductor chip on which the matrix of optical detectors is formed, the chip having a chip area determined by the lateral dimensions of the image sensor; and
- a chip package on which the chip is mounted, the package having a total area no greater than 200% of the chip area.

17. The endoscope according to claim 15, wherein the image sensor comprises a semiconductor chip on which the matrix of optical detectors is formed, wherein the chip is thinned following fabrication of the optical detectors on the chip.

18. The endoscope according claim 15, and comprising one or more light emitting diodes (LEDs) mounted at the distal end of the insertion tube so as to illuminate the object.

19. The endoscope according to claim 18, and comprising an electronic circuit board, which comprises a first mounting area on which the image sensor is mounted, and a second mounting area on which the one or more LEDs are mounted, wherein the second mounting area is angled relative to the first mounting area.

20. The endoscope according to claim 15, and comprising a light source located proximally to the distal end of the insertion tube, and a light guide, which passes through the insertion tube so as to emit light from the distal end of the tube to illuminate the object.

21. The endoscope according to claim 20, wherein the endoscope comprises a handle, and wherein the light source comprises at least one light-emitting diode disposed within the handle.

22. The endoscope according to claim 21, wherein the at least one light-emitting diode comprises a white-light light-emitting diode.

23. The endoscope according to claim 20, wherein the light guide comprises an optical fiber.

24. The endoscope according to claim 20, wherein the light source comprises a an array of light emitting diode (LEDs), and wherein the light guide comprises an array of optical fibers, which are respectively coupled to the LEDs so as to convey the radiation to the distal end of the endoscope in order to illuminate the object.

25. The endoscope according to claim 15, wherein the image sensor comprises a complementary metal oxide semiconductor device.

26. The endoscope according to claim 15, wherein the image sensor comprises a charge coupled device.

27. An endoscope, comprising:
- an insertion tube having a longitudinal axis and a distal end; and
- an electronic imaging device, mounted within the distal end of the insertion tube, and comprising:
  - an optical objective for collecting optical radiation from an object, the objective having an optical axis, which is substantially parallel to the longitudinal axis of the insertion tube;
  - an image sensor, comprising a planar matrix of optical detectors arranged in a plane that is substantially parallel to the optical axis, the image sensor having an active area, which has a lateral dimension in the plane;
  - a prism, having an exit face adjacent to the image sensor and an entrance face adjacent to the objective, and an optical surface comprising a reflective face of the prism, wherein the optical surface is positioned so as to reflect the radiation collected by the objective in order to form a focused image in the plane of the image sensor, while a maximum distance among distances from points on the optical surface to the plane of the image sensor is substantially less than the lateral dimension of the active area of the image sensor;
  - an aperture stop placed in front of the entrance face; and
  - wherein a surface of the prism opposite the exit face is flattened parallel to the exit face so as to reduce a height of the entrance face of the prism, and the aperture stop is placed close to the entrance face so that the height is substantially less than the lateral dimension of the active area of the image sensor.

28. The endoscope according to claim 27, wherein the insertion tube has a proximal end, and comprising a solid-state light source disposed at the proximal end of the insertion tube and adapted for directing radiation through the distal end toward the object.

29. The endoscope according to claim 28, and comprising a handle coupled to the proximal end of the insertion tube, wherein the solid-state light source comprises at least one light-emitting diode disposed within the handle.

30. The endoscope according to claim 29, wherein the at least one light-emitting diode comprises a white-light light-emitting diode.

31. The endoscope according to claim 28, further comprising a light guide optically coupled to the solid-state light source and extending through the insertion tube to the distal end.

32. The endoscope according to claim 31, wherein the light guide comprises an optical fiber.

33. The endoscope according to claim 28, wherein the solid-state light source comprises a an array of light emitting diode (LEDs) and an array of optical fibers, which are respectively coupled to the LEDs so as to convey the radiation to the distal end of the insertion tube so as to illuminate the object.

34. The endoscope according to claim 27, wherein the image sensor comprises a complementary metal oxide semiconductor device.

35. The endoscope according to claim 27, wherein the image sensor comprises a charge coupled device.

36. An endoscope, comprising:
- an insertion tube having a longitudinal axis and a distal end; and
- an electronic imaging device, mounted within the distal end of the insertion tube, and comprising:
  - an optical objective for collecting optical radiation from an object, the objective having an optical axis, which is substantially parallel to the longitudinal axis of the insertion tube;

an image sensor oriented in a plane that is substantially parallel to the optical axis, and comprising:
a semiconductor chip comprising a planar monolithic array of optical detectors having an active area, which has a lateral dimension in the plane of the image sensor, and having a predetermined chip area; and
a chip package on which the chip is mounted, the package having a total area no greater than about 200% of the chip area; and
a prism, having an exit face adjacent to the image sensor and an entrance face adjacent to the objective, and an optical surface comprising a reflective face of the prism, wherein the optical surface is positioned so as to direct the radiation collected by the objective to form a focused image in the plane of the image sensor, while a maximum distance among distances from points on the optical surface to the plane of the image sensor is substantially less that the lateral dimension of the active area of the array of optical detectors;
an aperture stop placed in front of the entrance face; and
wherein a surface of the prism opposite the exit face is flattened parallel to the exit face so as to reduce a height of the entrance face of the prism and the aperture stop is placed close to the entrance face so that the height is substantially less than the lateral dimension of the active area of the array of optical detectors.

37. The endoscope according to claim 36, wherein the insertion tube has a proximal end, and comprising a solid-state light source disposed at the proximal end of the insertion tube and adapted for directing radiation through the distal end toward the object.

38. The endoscope according to claim 37, and comprising a handle coupled to the proximal end of the insertion tube, wherein the solid-state light source comprises at least one light-emitting diode disposed within the handle.

39. The endoscope according to claim 38, wherein the at least one light-emitting diode comprises a white-light light-emitting diode.

40. The endoscope according to claim 37, further comprising a light guide optically coupled to the solid-state light source and extending through the insertion tube to the distal end.

41. The endoscope according to claim 40, wherein the light guide comprises an optical fiber.

42. The endoscope according to claim 37, wherein the solid-state light source comprises a an array of light emitting diode (LEDs) and an array of optical fibers, which are respectively coupled to the LEDs so as to convey the radiation to the distal end of the insertion tube so as to illuminate the object.

43. The endoscope according to claim 36, wherein the image sensor comprises a complementary metal oxide semiconductor device.

44. The endoscope according to claim 36, wherein the image sensor comprises a charge coupled device.

45. An electronic imaging device, comprising:
first and second optical objectives for collecting optical radiation from an object, the objectives having respective first and second optical axes, which are mutually substantially parallel;
first and second image sensors, comprising respective planar matrices of optical detectors, which are arranged back-to-back in respective first and second planes that are substantially parallel to the optical axes, the image sensors having active areas, which have a lateral dimension in the respective planes;
first and second prisms, each having an exit face adjacent to the image sensor and an entrance face adjacent to the objective, and an optical surface comprising a reflective face of the prism, wherein the respective first and second optical surfaces are positioned so as to reflect the radiation collected by the first and second objectives, respectively, so as to form respective first and second images in the first and second planes of the image sensors, while a maximum distance among distances from points on the first optical surface to the first plane and from the second optical surface to the second plane is substantially less than the lateral dimension of the active area of the image sensors;
an aperture stop placed in front of the entrance face of each prism; and
wherein a surface of the prism opposite the exit face is flattened parallel to the exit face so as to reduce a height of the entrance face of the prism, and the aperture stop is placed close to the entrance face so that the height is substantially less than the lateral dimension of the active area of the image sensor.

46. The device according to claim 45, wherein the first and second image sensors are adapted to generate respective first and second electrical signals responsively to the optical radiation that is incident thereon, and comprising an image processor, which is coupled to receive the first and second electrical signals and to process the signals so as to produce a stereoscopic image of the object.

47. The device according to claim 45, and comprising a circuit board, having first and second sides, wherein the first and second image sensors are mounted respectively on the first and second sides of the circuit board.

48. The device according to claim 45, wherein the maximum distance is less than approximately 75% of the lateral dimension of the image sensors.

49. The device according to claim 45, wherein each of the first and second image sensors comprises:
a semiconductor chip on which the matrix of optical detectors is formed, the chip having a chip area determined by the lateral dimensions of the image sensor; and
a chip package on which the chip is mounted, the package having a total area no greater than 200% of the chip area.

50. The device according to claim 45, wherein the first and second image sensors comprise semiconductor chips on which the matrices of optical detectors are formed, wherein the chips are thinned following fabrication of the optical detectors on the chips.

51. An endoscope, comprising:
an insertion tube having a longitudinal axis and a distal end; and
an electronic imaging device, mounted within the distal end of the insertion tube, and comprising:
first and second optical objectives for collecting optical radiation from an object, the objectives having respective first and second optical axes, which are mutually substantially parallel;
first and second image sensors, comprising respective planar matrices of optical detectors, which are arranged back-to-back in respective first and second planes that are substantially parallel to the optical axes, the image sensors having active areas, which have a lateral dimension in the respective planes;
first and second prisms, each having an exit face adjacent to the image sensor and an entrance face adjacent to the objective, and an optical surface comprising a reflective face of the prism, wherein the respective first and second optical surfaces are positioned so as to reflect the radiation collected by the first and second objectives, respectively, so as to form respective first and second images in the first and second planes of the image sensors, while a maximum distance among distances from points on from the first optical surface to the first plane and from the second optical surface to the second plane is substantially less than the lateral dimension of the active area of the image sensor;

an aperture stop placed in front of the entrance face of each prism; and wherein a surface of the prism opposite the exit face is flattened parallel to the exit face so as to reduce a height of the entrance face of the prism, and the aperture stop is placed close to the entrance face so that the height is substantially less than the lateral dimension of the active area of the image sensor.

52. The endoscope according to claim 51, wherein the insertion tube has a proximal end, and comprising a solid-state light source disposed at the proximal end of the insertion tube and adapted for directing radiation through the distal end toward the object.

53. The endoscope according to claim 52, and comprising a handle coupled to the proximal end of the insertion tube, wherein the solid-state light source comprises at least one light-emitting diode disposed within the handle.

54. The endoscope according to claim 53, wherein the at least one light-emitting diode comprises a white-light light-emitting diode.

55. The endoscope according to claim 52, further comprising a light guide optically coupled to the solid-state light source and extending through the insertion tube to the distal end.

56. The endoscope according to claim 55, wherein the light guide comprises an optical fiber.

57. The endoscope according to claim 52, wherein the solid-state light source comprises a an array of light emitting diode (LEDs) and an array of optical fibers, which are respectively coupled to the LEDs so as to convey the radiation to the distal end of the insertion tube so as to illuminate the object.

58. The endoscope according to claim 51, wherein the first and second image sensors comprise complementary metal oxide semiconductor devices.

59. The endoscope according to claim 51, wherein the first and second image sensors comprise charge coupled devices.

60. Imaging apparatus, comprising:
a camera head; and
a light source, which comprises:
an array of light emitting diode (LEDs), which are adapted to generate optical radiation;
an array of optical fibers, having respective proximal and distal ends, wherein the proximal ends are respectively coupled to the LEDs so that each of the fibers receives the radiation emitted by a respective one of the LEDs, and the distal ends are arranged to convey the radiation to a vicinity of the camera head so as to illuminate the object; and
a controller, which is adapted to drive the LEDs to emit the optical radiation at different, respective intensities so as to adjust illumination of the object; and
wherein the camera head further comprises:
an optical objective for collecting optical radiation from an object, the objective having an optical axis;
an image sensor comprising a planar matrix of optical detectors arranged in a plane that is substantially parallel to the optical axis, the image sensor having an active area, which has a lateral dimension in the plane;
a prism, having an exit face adjacent to the image sensor and an entrance face adjacent to the objective, and an optical surface comprising a reflective face of the prism, wherein the optical surface is positioned so as to reflect the radiation collected by the objective in order to form a focused image in the plane of the image sensor, while a maximum distance among distances from points on the optical surface to the plane of the image sensor is substantially less than the lateral dimension of the active area of the image sensor;
an aperture stop placed in front of the entrance face; and
wherein a surface of the prism opposite the exit face is flattened parallel to the exit face so as to reduce a height of the entrance face of the prism, and the aperture stop is placed close to the entrance face so that the height is substantially less than the lateral dimension of the active area of the image sensor.

61. The apparatus according to claim 60, wherein the controller is adapted to drive the LEDs responsively to the image of the object, so as to adjust for uneven brightness in the image.

62. A method for electronic imaging, comprising:
aligning an optical objective to collect optical radiation from an object along an optical axis;
arranging an image sensor, comprising a planar matrix of optical detectors, in a plane that is substantially parallel to the optical axis, the image sensor having an active area, which has a lateral dimension in the plane;
positioning a prism, having an exit face adjacent to the image sensor and an entrance face adjacent to the objective, and an optical surface comprising a reflective face of the prism so that the optical surface of the prism reflects the radiation collected by the objective in order to form a focused image in the plane of the image sensor, such that a maximum distance among distances from points on the optical surface to the plane of the image sensor is substantially less than the lateral dimension of the active area of the image sensor;
positioning an aperture stop in front of the entrance face, and wherein a surface of the prism opposite the exit face is flattened parallel to the exit face so as to reduce a height of the entrance face of the prism, and the aperture stop is placed close to the entrance face so that the height is substantially less than the lateral dimension of the active area of the image sensor.

63. A method for electronic imaging, comprising:
aligning an optical objective for collecting optical radiation from an object along an optical axis;
orienting an image sensor in a plane that is substantially parallel to the optical axis, the image sensor comprising a semiconductor chip, which comprises a planar monolithic array of optical detectors having an active area, which has a lateral dimension in the plane of the image sensor and having a predetermined chip area and is mounted on a chip package having a total area no greater than about 200% of the chip area;
positioning a prism, having an exit face adjacent to the image sensor and an entrance face adjacent to the objective, and an optical surface comprising a reflective face of the prism, so as to direct the radiation collected by the objective to form a focused image in the plane of the image sensor, while a maximum distance among distances from points on the optical surface to the plane of the image sensor is substantially less that the lateral dimension of the active area of the array of optical detectors;

positioning an aperture stop in front of the entrance face, and wherein a surface of the prism opposite the exit face is flattened parallel to the exit face so as to reduce a height of the entrance face of the prism and the aperture stop is placed close to the entrance face so that the height is substantially less than the lateral dimension of the active area of the array of optical detectors.

64. A method for endoscopic imaging, comprising:

providing an insertion tube of predetermined diameter, the tube having a longitudinal axis and a distal end;

fixing an image sensor within the insertion tube, the image sensor comprising a planar matrix of optical detectors arranged in a plane that is substantially parallel to the longitudinal axis, the image sensor having an active area, which has a lateral dimension in the plane and a diagonal dimension in the plane that is substantially greater than the diameter of the insertion tube; and aligning imaging optics adjacent to the distal end of the tube, so as to focus optical radiation from an object onto the image sensor in order to form an image of the object on the image sensor; and wherein the imaging optics comprise:

an optical objective for collecting the optical radiation from the object;

a prism, having an exit face adjacent to the image sensor and an entrance face adjacent to the objective, and an optical surface comprising a reflective face of the prism, wherein the optical surface is positioned so as to reflect the radiation collected by the objective in order to form a focused image in the plane of the image sensor, while a maximum distance among distances from points on the optical surface to the plane of the image sensor is substantially less than the lateral dimension of the active area of the image sensor;

an aperture stop placed in front of the entrance face; and wherein a surface of the prism opposite the exit face is flattened parallel to the exit face so as to reduce a height of the entrance face of the prism, and the aperture stop is placed close to the entrance face so that the height is substantially less than the lateral dimension of the active area of the image sensor.

65. An endoscope, having distal and proximal portions, and comprising:

an optical objective for collecting radiation from an object, the objective being disposed in the distal portion of the endoscope and having an optical axis;

an image sensor comprising a planar matrix of optical detectors arranged in a plane that is substantially parallel to the optical axis, the image sensor having an active area, which has a lateral dimension in the plane;

a prism, having an exit face adjacent to the image sensor and an entrance face adjacent to the objective, and an optical surface comprising a reflective face of the prism, wherein the optical surface is positioned to reflect the radiation collected by the objective in order to form an image on the plane of the image sensor, while a maximum distance among distances from points on the optical surface to the plane of the image sensor is substantially less than the lateral dimension of the active area of the image sensor;

an aperture stop placed in front of the entrance face;

wherein a surface of the prism opposite the exit face is flattened parallel to the exit face so as to reduce a height of the entrance face of the prism, and the aperture stop is placed close to the entrance face so that the height is substantially less than the lateral dimension of the active area of the image sensor; and a solid-state light source disposed within the proximal portion of the endoscope and adapted for directing radiation through the distal portion toward the object.

66. The endoscope according to claim 65, wherein the proximal portion of the endoscope comprises a handle, and wherein the solid-state light source comprises at least one light-emitting diode disposed within the handle.

67. The endoscope according to claim 66, wherein the light-emitting diode comprises a white-light light-emitting diode.

68. The endoscope according to claim 65, further comprising a light guide optically coupled to the solid-state light source and extending through the endoscope to the distal portion.

69. The endoscope according to claim 68, wherein the light guide comprises an optical fiber.

70. The endoscope according to claim 65, wherein the image sensor comprises a complementary metal oxide semiconductor device.

71. The endoscope according to claim 65, wherein the image sensor comprises a charge coupled device.

72. The endoscope according to claim 65, wherein the solid-state light source comprises a an array of light emitting diode (LEDs) and an array of optical fibers, which are respectively coupled to the LEDs so as to convey the radiation to the distal portion of the endoscope in order to illuminate the object.

* * * * *